(12) United States Patent
Kaldany

(10) Patent No.: US 7,351,257 B2
(45) Date of Patent: Apr. 1, 2008

(54) VASCULAR GRAFT DEVICE

(75) Inventor: Antoine Kaldany, Chestnut Hill, MA (US)

(73) Assignee: InterMed, Inc., Chestnut Hill, MA (US)

( * ) Notice: Subject to any disclaimer, the term of this patent is extended or adjusted under 35 U.S.C. 154(b) by 693 days.

(21) Appl. No.: 10/822,217

(22) Filed: Apr. 9, 2004

(65) Prior Publication Data

US 2004/0265352 A1    Dec. 30, 2004

Related U.S. Application Data

(60) Provisional application No. 60/463,891, filed on Apr. 17, 2003.

(51) Int. Cl.
*A61F 2/06* (2006.01)

(52) U.S. Cl. ...................................... 623/1.27

(58) Field of Classification Search .............. 623/1.27, 623/66.1; 424/423
See application file for complete search history.

(56) References Cited

U.S. PATENT DOCUMENTS

| | | | |
|---|---|---|---|
| 5,049,131 A | 9/1991 | Deuss | |
| 5,370,681 A * | 12/1994 | Herweck et al. | 623/1.27 |
| 5,411,550 A * | 5/1995 | Herweck et al. | 623/1.27 |
| 5,893,840 A | 4/1999 | Hull et al. | |
| 6,010,480 A | 1/2000 | Abele et al. | |
| 6,187,038 B1 * | 2/2001 | Sullivan et al. | 623/1.43 |
| 6,613,084 B2 * | 9/2003 | Yang | 623/1.42 |
| 6,659,996 B1 | 12/2003 | Kaldany | |
| 6,926,735 B2 * | 8/2005 | Henderson | 623/1.42 |
| 6,939,374 B2 * | 9/2005 | Banik et al. | 623/1.27 |

* cited by examiner

*Primary Examiner*—Sharon E. Kennedy
(74) *Attorney, Agent, or Firm*—Hamilton, Brook, Smith & Reynolds, P.C.

(57) ABSTRACT

A vascular graft device includes a semipermeable inner wall surrounding a passage. A nonpermeable outer wall surrounds the inner wall. A biological agent is disposed between the inner and outer walls for release through the inner wall.

23 Claims, 3 Drawing Sheets

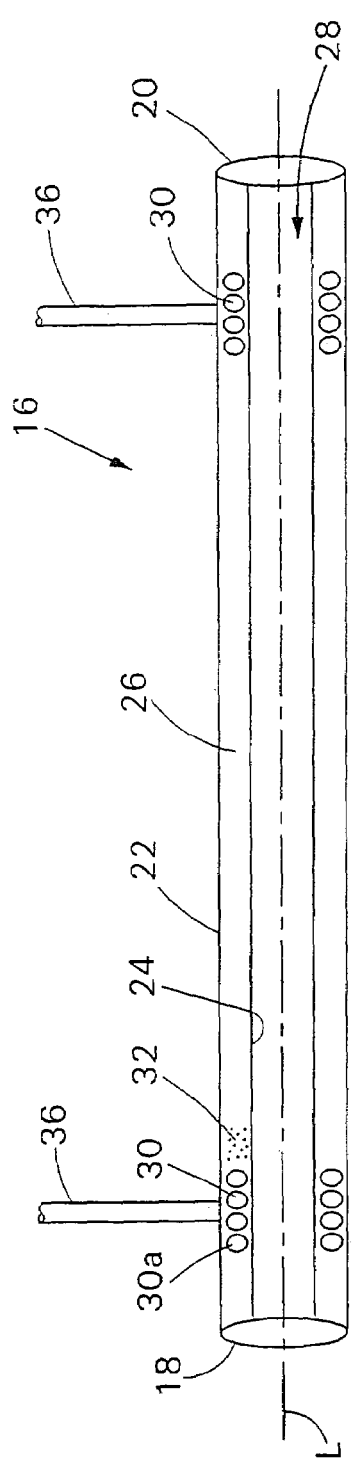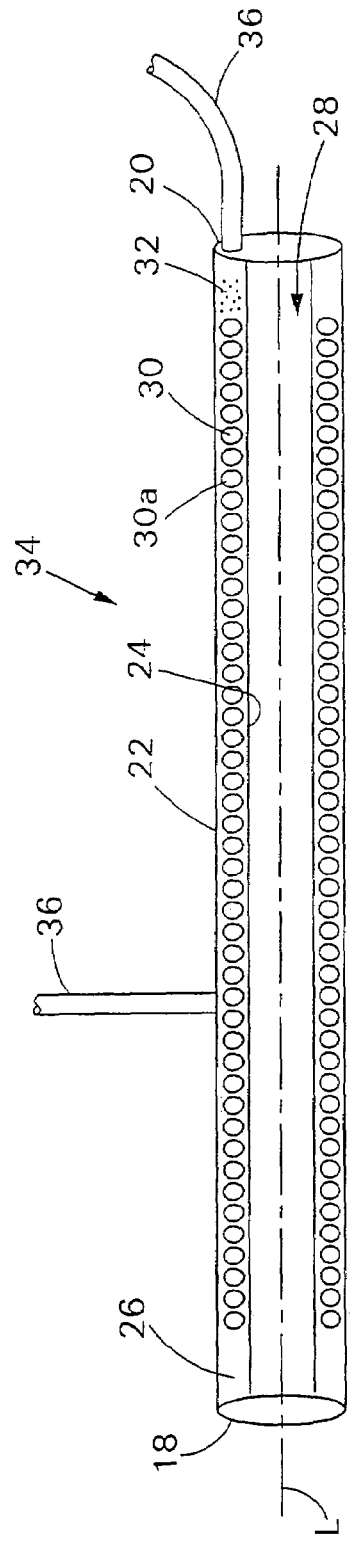

VASCULAR GRAFT DEVICE

RELATED APPLICATION

This application claims the benefit of U.S. Provisional Application No. 60/463,891, filed Apr. 17, 2003. The entire teachings of the above application(s) are incorporated herein by reference.

BACKGROUND

Almost a million patients undergo chronic hemodialysis, the majority of whom are in the U.S. Typically patients are connected to dialysis machinery through a needle. Since a patient's blood vessels are not able to withstand repeated access with a needle, often vascular access is provided through a polytetrafluoroethylene (PTFE) graft, or another biocompatible vessel like a conduit such as a bovine vein graft, etc., that is sutured to a blood vessel. About 70% of such patients require two or more dialysis vascular access replacements and/or repairs every year. The annual cost of maintaining a single patient on hemodialysis in the U.S. is about $48,000 per year. More than 30% of this cost is related to the creation and maintenance of the dialysis vascular access. One problem occurring in vascular access grafts is that the overgrowth of cells in the vascular wall occurring at the suture points can lead to occlusion. Such overgrowth is at its highest during the first six months after the implantation or the repair of the graft.

SUMMARY

The present invention provides a vascular graft device which in some embodiments can have limited or reduced occlusion. A particular embodiment includes a vascular graft device having a semipermeable inner wall surrounding a passage. A nonpermeable outer wall surrounds the inner wall. A biological agent is disposed between the inner and outer walls for release through the inner wall.

In particular embodiments, the biological agent can include a time release drug which can be in a microencapsulated form within a gelatinous media. Some time release drugs can prevent occlusion. In other embodiments, the biological agent can include cells. In some applications, the graft device can function as an artificial organ.

The graft device can be generally tubular in shape and the outer wall can be sealed to the inner wall at first and second ends of the graft device. The outer wall can be made of PTFE. The graft device is capable of being sutured to at least one blood vessel at the first and second ends. The biological agent is typically positioned at least near the first and second ends of the graft device. A conduit can extend from the graft device for replenishing or refilling the biological agent. In other embodiments, a tubular inner graft member having first and second ends for suturing to at least one blood vessel can be positioned within the passage of the vascular graft device.

The present invention also provides a method of limiting occlusion in a vascular graft device including providing the vascular graft device with a semipermeable inner wall surrounding a passage. The inner wall is surrounded with a nonpermeable outer wall. A biological agent is disposed between the inner and outer walls for time release through the inner wall. The time release of the biological agent limits or reduces occlusion over a period of time.

The present invention also provides a vascular device including an inner wall surrounding a passage. An outer wall surrounds the inner wall with a gap therebetween. A biological agent is disposed between the inner and outer walls and is capable of being released.

BRIEF DESCRIPTION OF THE DRAWINGS

The foregoing and other objects, features and advantages of the invention will be apparent from the following more particular description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 2 is a side schematic view of the vascular graft device of FIG. 1.

FIG. 3 is a side schematic view of another embodiment of a vascular graft device.

DETAILED DESCRIPTION

Figure 1:
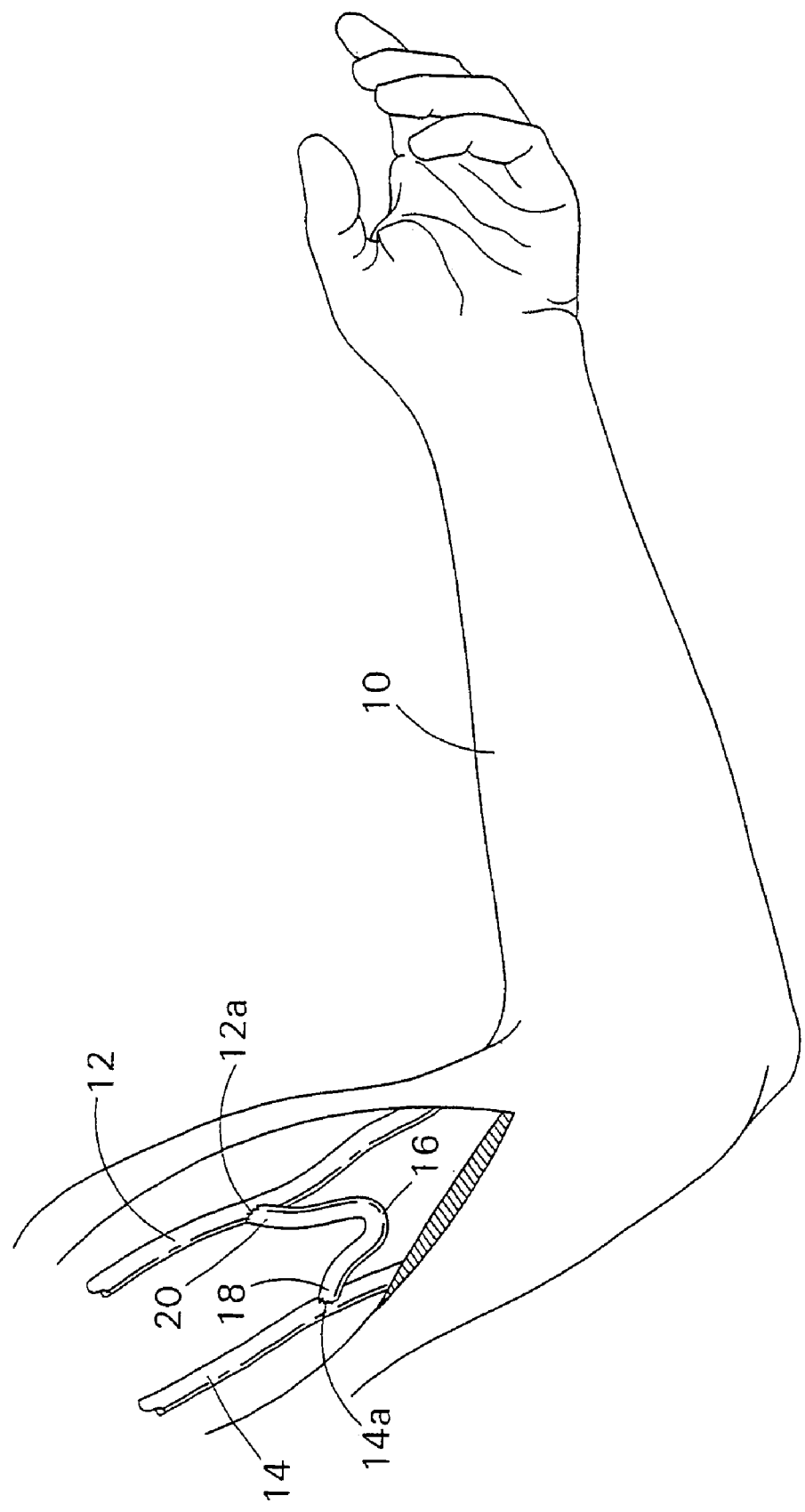
FIG. 1 is a schematic drawing of an embodiment of a vascular graft device in the present invention implanted in an arm of a patient and sutured to a vein and to an artery.

Referring to FIG. 1, a vascular graft device 16 in the present invention can be implanted into a patient to provide vascular access to a dialysis machine (not shown). A needle in communication with the dialysis machine with tubing can be inserted into the vascular graft device 16 instead of the patient's blood vessels. In the example shown in FIG. 1, a first end 18 of the vascular graft device 16 is sutured to a location 14a of an artery 14 in an arm 10, and a second end 20 is sutured to a location 12a of a vein 12. The vascular graft device 16 can be also implanted in other suitable locations of the patient for communication with other blood vessels. The vascular graft device 16 is typically located under the skin of the patient.

In the embodiment shown in FIG. 2, the vascular graft device 16 is generally tubular and elongate in shape with a central passage 28 extending therethrough along a central axis L for communication with the blood vessels to which the ends 18 and 20 are sutured. As seen in FIG. 1, when implanted, the vascular graft device 16 can be bent. The vascular graft device 16 has an inner semipermeable wall 24 which surrounds the central passage 28 and a nonpermeable outer wall 22 spaced apart from and surrounding the inner wall 24 to form a gap 26 or reservoir region therebetween. The gap 26 can be generally annular in shape. The inner wall 24 and the outer wall 22 are typically sealed at the ends 18 and 20. Such sealing can be accomplished by sealing the inner wall 24 directly to the outer wall 22 or through an intermediate component and/or sealant. The outer wall 22 can be made of polytetrafluoroethylene (PTFE) or similar biocompatible material, for example, bovine vein grafts, etc.

A biological agent 30 is disposed within the gap 26 of the vascular graft device 16 at least near the ends 18 and 20, for example, in two annular rings, as shown. The term "biological agent" is meant to encompass any substance that can be introduced into tissue or a body cavity for treating a patient such as drugs, microspheres, cells, cell clusters, cells transfected with foreign DNA, cellular components, cellular extracts or gene products. The biological agent 30 can include a gelatinous self-sealing media 32 in which portions 30a of the biological agent 30 are interdispersed. In some embodiments, the gelatinous media 32 can be used to provide sealing of the ends 18 and 20 between the inner 24 and outer 22 walls. FIG. 2 depicts the portions 30a of the biological agent 30 being microspheres, but it is understood that the portions 30a can have many different configurations depending upon the biological agent 30, for example, cell clusters, or liquid interdispersed within the gelatinous media 32. In some embodiments, a liquid such as saline can be used instead of the gelatinous media 32.

In the configuration depicted in FIG. 2, the biological agent 30 can be a time release microencapsulated drug which is released over an extended time for resisting occlusion of the vascular graft device 16 and/or the blood vessels at the suture points. The nonpermeable outer wall 22 prevents release of the biological agent 30 outwardly so that delivery of the biological agent 30 can be generally directed radially inwardly in a circular fashion through the semipermeable inner wall 22 into the passage 28 near the ends 18 and 20. One or more refill conduits 36 in communication with the gap 26 can extend up to the subcutaneous layers of the patient for periodic replenishment of the biological agent 30, including the gelatinous media 32, as needed. Depending upon the biological agent 30 used and the number of refills performed, time release of drugs for reducing occlusion can extend well beyond the typical six weeks achieved with prior art grafts that have an external drug coating. For example, occlusion reducing drugs can be released for six months, which is about the time period in which most occlusion usually occurs.

Referring to FIG. 3, vascular graft device 34 differs from graft device 16 in that the biological agent 30 extends about the whole length of the vascular graft device 34 in an annular fashion for release of the biological agent 30 radially inwardly in a circular fashion along the length of passage 28. In addition, one or more refill conduits 36 in communication with gap 26 can extend from the lateral side or the longitudinal ends of the vascular graft device 34. The gap 26 can be filled with more than one type of biological agent 30, for example, positioning occlusion resistant drugs near the ends 18 and 20, and biological agents 30 for other purposes in the intermediate regions, for example, therapeutic, antibiotic, behavioral, mental health or addiction drugs/biological agents. If desired, the gap 26 can include partitions for separating the different biological agents.

Figure 4:
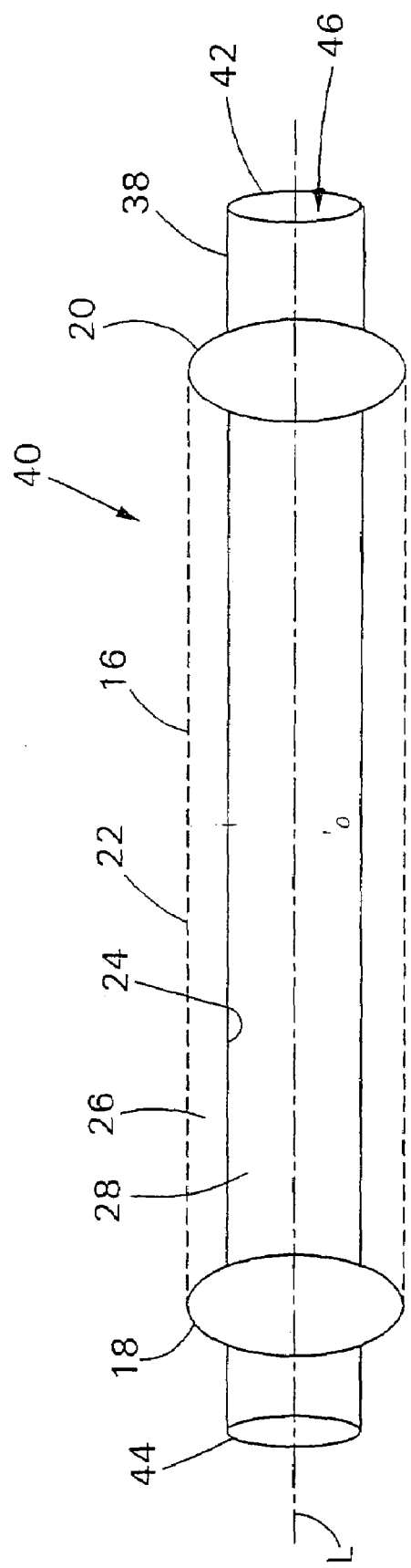
FIG. 4 is a side schematic view of yet another embodiment of a vascular graft device.

Referring to FIG. 4, vascular graft device 40 includes an inner graft member 38 having a central passage 46 which is inserted into the central passage 28 of vascular device 16, and which forms an outer ring around the inner graft member 38. The inner graft member 38 can be a conventional vascular graft member which is sutured to blood vessels at the ends 42 and 44. The vascular device 16 can be configured to release the biological agent 30 longitudinally from the ends 18 and 20 in an annular or circular pattern. In other embodiments, the inner graft member 38 can be semipermeable so that the biological agent 30 can enter the passage 46 laterally or radially inwardly in a circular fashion through the wall of inner graft member 38. In such an embodiment, the inner wall 24 of the vascular device 16 can be omitted. In still other embodiments, vascular device 16 can be replaced with vascular device 34 in whole or in part.

The embodiments depicted in FIGS. 2-4 and described above can also be employed as an artificial organ by seeding cells in a bioactive layer within the gap 26. For example, insulin secreting islet cells can be used to form an artificial pancreas. In addition, if adequate numbers of liver cells are utilized in a suitably sized graft, an ectopic artificial liver can be formed for cleaning/metabolizing liver toxins. Animal cells can also be used to deliver specific biological functions.

The inner walls of the devices can be made of material which separates the cells from the bloodstream to act as an immunological barrier and improve biocompatibility. For such uses, the devices may be configured in shapes that are non-tubular and have multiple and/or tortuous passages for increasing the surface area for biological exchange.

While this invention has been particularly shown and described with references to particular embodiments thereof, it will be understood by those skilled in the art that various changes in form and details may be made therein without departing from the scope of the invention encompassed by the appended claims.

For example, features of the embodiments described above can be omitted or combined. In addition, one or more intermediate semipermeable or permeable walls can be positioned between the inner wall 24 and the outer wall 22. Gap 26 can have enlarged regions for increased capacity, or auxiliary reservoirs can be connected to gap 26. The biological agents 30 do not have to be positioned in an annular fashion within gap 26 but can also be positioned on one side, or more than one side. In some cases, the vascular devices may be sutured to a single blood vessel, such as for replacing a section or bypassing a section of the blood vessel. Embodiments of the vascular devices in the present invention can also be used as a stent, and one or both walls can be rigid, or hardenable, for example, by radiation such as ultraviolet (UV) light. In some embodiments, one or both of the inner and outer walls can be either nonpermeable or semipermeable. If both the inner and outer walls are nonpermeable, the ends of the inner and outer walls are not sealed so that the biological agent can be delivered from the ends.

What is claimed is:

1. A vascular graft device comprising:
   a semi permeable inner wall surrounding a passage;
   a nonpermeable outer wall surrounding the inner wall, the graft device being configured for access by a needle and being longitudinally bendable and having first and second ends, the inner and outer walls being sealed to each other at the first and second ends, forming an annular gap between the inner and outer walls, the first and second ends each being configured for suturing to at least one blood vessel; and
   a biological agent disposed between the inner and outer walls for release through the inner wall radially inwardly in a circular fashion at least near the first and second ends for treating suture points joining the at least one blood vessel at the first and second ends.

2. The graft device of claim 1 in which the biological agent comprises a time release drug.

3. The graft device of claim 2 in which the time release drug is for preventing occlusion.

4. The graft device of claim 2 in which the biological agent comprises microencapsulated drugs within a gelatinous media.

5. The graft device of claim 1 in which the biological agent comprises cells.

6. The graft device of claim 5 in which the graft device functions as an artificial organ.

7. The graft device of claim 1 in which the graft device is generally tubular in shape.

8. The graft device of claim 7 in which the outer wall comprises PTFE.

9. The graft device of claim 1 in which the biological agent is positioned at least near the first and second ends of the graft device.

10. The graft device of claim 7 further comprising a tubular inner graft member positioned within the passage of the vascular graft device, the inner graft member having first and second ends for suturing to at least one blood vessel.

11. The graft device of claim 1 further comprising a conduit extending from the graft device for replenishing the biological agent.

12. A vascular graft device comprising:
a semi permeable inner wall surrounding a passage;
a nonpermeable outer wall surrounding the inner wall and sealed to the inner wall at first and second ends of the graft device such that the graft device is generally tubular in shape, the graft device being configured for access by a needle and being longitudinally flexible and the first and second ends of the graft device each being configured for suturing to at least one blood vessel; and
a biological agent disposed between the inner and outer walls at least near the first and second ends for release through the inner wall radially inwardly in a circular fashion at least near the first and second ends for treating suture points joining the at least one blood vessel at the first and second ends.

13. A vascular graft device comprising:
an inner wall surrounding a passage;
an outer wall surrounding the inner wall with a gap therebetween;
a biological agent disposed between the inner and outer walls capable of being released; and
an inner graft member positioned within the passage of the inner wall, the inner graft member having first and second ends extending beyond the inner and outer walls for suturing to at least one blood vessel.

14. A method of forming a vascular graft device comprising:
providing a semi permeable inner wall surrounding a passage;
surrounding the inner wall with a nonpermeable outer wall, the graft device being configured for access by a needle and being longitudinally bendable and having first and second ends, the inner and outer walls being sealed to each other at the first and second ends, forming an annular gap between the inner and outer walls, the first and second ends each being configured for suturing to at least one blood vessel; and
disposing a biological agent between the inner and outer walls for release through the inner wall radially inwardly in a circular fashion at least near the first and second ends for treating suture points joining the at least one blood vessel at the first and second ends.

15. The method of claim 14 further comprising providing a time release drug as the biological agent.

16. The method of claim 14 further comprising providing microencapsulated drugs within a gelatinous media as the biological agent.

17. The method of claim 14 further comprising providing cells as the biological agent.

18. The method of claim 14 further comprising forming the graft device to be generally tubular in shape.

19. The method of claim 18 further comprising forming the outer wall from PTFE.

20. The method of claim 14 further comprising positioning the biological agent at least near the first and second ends of the graft device.

21. The method of claim 18 further comprising positioning a tubular inner graft member within the passage of the vascular graft device, the inner graft member having first and second ends for suturing to at least one blood vessel.

22. The method of claim 14 further comprising extending a conduit from the graft device for replenishing the biological agent.

23. A method of limiting occlusion in a vascular graft device comprising:
providing the vascular graft device with a semi permeable inner wall surrounding a passage;
surrounding the inner wall with a nonpermeable outer wall, the graft device being configured for access by a needle and being longitudinally bendable and having first and second ends, the inner and outer walls being sealed to each other at the first and second ends, forming an annular gap between the inner and outer walls, the first and second ends each being configured for suturing to at least one blood vessel; and
disposing a biological agent between the inner and outer walls for time release through the inner wall radially inwardly in a circular fashion at least near the first and second ends for treating suture points joining the at least one blood vessel at the first and second ends, the time release of the biological agent for limiting occlusion over a period of time.

* * * * *